(12) United States Patent
Bazarov et al.

(10) Patent No.: US 7,111,516 B2
(45) Date of Patent: Sep. 26, 2006

(54) IN-TUBE ULTRASONIC DEVICE FOR WALL THICKNESS METERING

(75) Inventors: Alexandr J. Bazarov, Kolomna (RU);
Alexandr P. Desyatchikov, Kolomna (RU); Nikolai A. Karasev, Kolomna (RU); Sergei P. Kirichenko, Kolomna (RU); Andrei M. Slepov, Kolomna (RU); Anatoly V. Smirnov, Kolomna (RU); Sergei N. Hrapov, Kolomna (RU)

(73) Assignee: NGKS International Corporation, Ontario (CA)

( * ) Notice: Subject to any disclaimer, the term of this patent is extended or adjusted under 35 U.S.C. 154(b) by 970 days.

(21) Appl. No.: 10/199,499

(22) Filed: Jul. 22, 2002

(65) Prior Publication Data

US 2003/0083576 A1     May 1, 2003

(30) Foreign Application Priority Data

Oct. 25, 2001   (RU) ............................... 2001128695

(51) Int. Cl.
*G01N 29/04*     (2006.01)
(52) U.S. Cl. ....................................... 73/623
(58) Field of Classification Search ............... 73/623, 73/622, 602, 1.82, 866.5; 377/24.1
See application file for complete search history.

(56) References Cited

U.S. PATENT DOCUMENTS

| | | | |
|---|---|---|---|
| 3,882,606 A * | 5/1975 | Kaenel et al. ................. | 33/544 |
| 4,137,639 A * | 2/1979 | Zumbach .................. | 33/501.02 |
| 4,162,635 A | 7/1979 | Triplett et al. | |

(Continued)

FOREIGN PATENT DOCUMENTS

RU     2018817     8/1994

(Continued)

*Primary Examiner*—Hezron Williams
*Assistant Examiner*—Jacques M. Saint-Surin
(74) *Attorney, Agent, or Firm*—Venable, LLP; James R. Burdett

(57) ABSTRACT

What is claimed is an inspection device for in-tube monitoring of main pipelines by the method of ultrasonic wall thickness metering realized in a device traveling inside the pipeline and performing measurements, acquisition of measurement data and their interpretation. The device comprises a probing pulse generator, an ultrasonic transducer, an amplifier, a comparator with an analog input, a digital timer, a processor and a data storage module, and a controlled reference voltage source connected in series. The output of said reference voltage source is connected to the reference voltage input of the comparator, said reference voltage source being capable of setting at least two different voltages at its output.

The comparator output is connected to one of the control inputs of the reference voltage source that allows one to switch threshold values in the comparator, when recording the ultrasonic pulses, to use one threshold value to record the moment of reception of the ultrasonic pulse reflected from the internal wall of the pipeline using another threshold value of the comparator to record the moment of reception of the ultrasonic pulse reflected from the external wall of the pipeline using the other threshold value. Thus, the operator can perform direct measurements of the transit time of the ultrasonic pulses in the pipe wall allowing him to increase the distance monitored per one pass of the device, and to increase the accuracy of measurements and the rate of hardware data processing compared to the prototypes known in the art.

20 Claims, 5 Drawing Sheets

U.S. PATENT DOCUMENTS

| | | | |
|---|---|---|---|
| 4,747,317 A * | 5/1988 | Lara ........................... 73/865.8 |
| 4,909,091 A | 3/1990 | Ellmann et al. |
| 4,964,059 A | 10/1990 | Sugaya et al. |
| 5,062,300 A | 11/1991 | Vallee |
| 5,088,336 A * | 2/1992 | Rosenberg et al. ........ 73/865.8 |
| 5,460,046 A | 10/1995 | Maltby et al. |
| 5,497,661 A | 3/1996 | Stripf et al. |
| 5,587,534 A | 12/1996 | McColskey et al. |
| 5,635,645 A | 6/1997 | Ottes et al. |
| 6,571,634 B1 * | 6/2003 | Bazarov et al. ............... 73/623 |
| 6,651,503 B1 * | 11/2003 | Bazarov et al. ............... 73/623 |
| 6,772,637 B1 * | 8/2004 | Bazarov et al. ............... 73/623 |

FOREIGN PATENT DOCUMENTS

| | | |
|---|---|---|
| RU | 2042946 | 8/1995 |
| RU | 2108569 | 4/1998 |

* cited by examiner

IN-TUBE ULTRASONIC DEVICE FOR WALL THICKNESS METERING

BACKGROUND OF THE INVENTION

The present invention relates to devices for flaw detection of long-distance pipelines, mainly trunk oil pipelines, oil-products pipelines and gas pipelines, by providing acoustic coupling between the ultrasonic transducers and the pipe walls (for example, with the help a fluid plug) and using the method of thickness metering and a so-called "pig" or a scanning device which is put into the pipeline and transported under power of the fluid flow in the pipeline. The scanning pig has built-in transducers, means for measurement, conversion and recording of the measured data and a device for collecting the digital data in the process of pig travel and for processing the obtained data to detect the flaws in the pipe walls and to determine the parameters of the detected flaws, as well as their location in the pipeline.

Known in the art is a device for in-tube flaw detection [RU2018817, RU2042946, RU2108569, U.S. Pat. No. 4,162,635], comprising a body with a built-in equipment for measurement, processing and storage of the measured data, said device including ultrasonic transducers.

When traveling inside the pipeline, this device emits probing pulses and receives the corresponding reflected ultrasonic pulses. The characteristics of the received ultrasonic pulses are used for determining the flaws in the pipeline.

Also known in the art is a device for in-tube flaw detection [U.S. Pat. No. 5,587,534, (relevant patent documents: CA2179902, EP0741866, AU4234596, JP3058352), U.S. Pat. No. 4,964,059, (relevant patent documents: CA1292306, EP0304053, NO304398, JP1050903), U.S. Pat. No. 5,062,300, (relevant patent documents: CA1301299, EP0318387, DE3864497, FR2623626, JP2002923)] comprising a housing incorporating equipment for measurement, processing and storage of the measured data, said equipment comprising a probing pulse generator, an ultrasonic transducer, a pulse processing module, a timer, a processor and a data storage module connected in series.

The device travels inside the pipeline, emits probing pulses towards the pipe wall and receives the respective ultrasonic pulses reflected from the internal and external walls of the pipeline while measuring the transit time of said ultrasonic pulses.

Known in the art is a device for in-tube flaw detection [U.S. Pat. No. 4,909,091, (relevant patent documents: CA1303722, EP0271670, DE3638936, NO302322, JP63221240), U.S. Pat. No. 5,635,645, (relevant patent documents: WO9312420, CA2125565, EP0616692, DE4141123, JP2695702)] comprising a housing incorporating equipment for measurement, processing and storage of the measured data, said equipment comprising a probing pulse generator, an ultrasonic transducer, a pulse processing module, a timer, a processor and a data storage module connected in series.

When traveling inside the pipeline, the device emits probing pulses and receives the respective ultrasonic pulses reflected from the internal and external walls of the pipeline while measuring the transit time of the ultrasonic pulse reflected from the internal wall of the pipeline, the transit time of the ultrasonic pulse reflected from the internal wall, the transit time of the ultrasonic pulse reflected from the external wall. The difference between these values is determined and the obtained data are recorded in the data storage module.

However, the measurement of the pulse transmit time to an external wall of the pipe and back with a given accuracy requires the use of a digital data sharper with a word length greater than in the case of direct measurement of the ultrasonic pulse transit time in a pipe wall (the speed of propagation of ultrasound in a fluid medium is much less than its speed in the pipeline material) This difference is especially significant when metering the thickness of thin-walled pipelines, in which the thickness of the pipe wall can be much less than distance from the transducer to the internal wall of the pipeline.

The measurements with an accuracy sufficient for detection and identification of the flaws and for determination of their parameters requires the use of large-capacity storage devices, whereas the pig moving inside the pipeline has a limited space for data storage devices.

Known in the art is a device for in-tube flaw detection [U.S. Pat. No. 5,460,046, (relevant patent documents: EP0684446, JP7318336)] comprising a housing incorporating equipment for measurement, processing and storage of the measured data, said equipment comprising a probing pulse generator, an ultrasonic transducer, a pulse processing module, a timer, a processor and a data storage module connected in series.

The device travels inside the pipeline, emits probing pulses during its movement and receives the respective ultrasonic pulses reflected from the internal and external walls of the pipeline while measuring the transmit time of the ultrasonic pulse in the pipe wall. The values corresponding to the pipe thickness within permissible limits are neglected, and the values corresponding to the wall thickness outside of the permissible thickness are recorded.

The use of the above device allows one to carry out direct measurement of the time interval between the reception of the ultrasonic pulse reflected from the internal wall of the pipeline and the reception of the ultrasonic pulse reflected from the external wall of the pipeline.

However, the absence of data on the greater part of the length of the monitored pipeline makes it difficult to interpret the data loss, for example, because of poor cleaning of the inner space of the pipeline from paraffin before passing the inspection pig or because of a paraffin deposit on the pipe walls during the travel of the inspection pig through a pipeline filled with heavy oils.

The prototype of the present invention is a device for in-tube ultrasonic thickness metering [U.S. Pat. No. 5,497,661, (relevant patent documents: WO92 10746, CA2098480, EP0561867, DE4040190)], including a housing accommodating equipment for measurements, processing and storage of the measured data, said equipment including a probing pulse generator, an ultrasonic transducer, an amplifier, a comparator with an analog input and with a preset threshold adjusted for recording the ultrasonic pulse reflected from the internal wall of the pipeline, a digital timer, a processor and a data storage module connected in series.

The device is characterized by the presence of an analog-to-digital converter, a buffer memory, and digital data processing modules.

The device travels inside the pipeline, emits probing ultrasonic pulses and receives the corresponding ultrasonic pulses reflected from the internal and external walls of the pipeline. The time interval between the reception of the first ultrasonic pulse reflected from the internal wall of the pipeline and the reception of the second ultrasonic pulse reflected from the external wall of the pipeline are measured. The instants of reception of the first and second ultrasonic pulses are determined, when the electric pulse corresponding to the first or second ultrasonic pulse reaches a threshold value. The electric pulses are digitized by amplitude with a frequency of 28 MHz and resolution of 8 bits. A threshold is set in the analog comparator using the change of state at the comparator output in response to an input signal corresponding to received ultrasonic pulses for starting the operations of quantization of pulses and processing of the obtained digital data. The converted digital data are recorded in a data storage module.

The storage of the information on the shape of the electric pulses or on the amplitudes of the electric signals and instants of time corresponding to these amplitudes in a memory device increases the efficiency of interpretation of the data obtained on the waxed sections of the pipelines characterized by high attenuation of the ultrasonic pulses. However, this also increases the volume of data per given length of the pipeline, which should be stored in the memory device having a limited capacity. As a result, it makes it necessary to decrease the distance to be inspected per pass of the inspection pig.

SUMMARY OF THE INVENTION

In an exemplary embodiment, the device for in-tube ultrasonic thickness metering traveling inside the pipeline being inspected, like the prototype, has a housing incorporating equipment for measurements, processing and storage of the measured data, said equipment including a probing pulse generator, an ultrasonic transducer, an amplifier, a comparator with an analog input, a digital timer, a processor and a data storage module.

In contrast, to the prototype, the device further comprises a controlled source of reference voltage, whose output is connected to the input of reference voltage of the comparator; the reference voltage source has an output with at least two values of reference voltage and has a first control input for setting a first reference voltage at the output and a second control input for setting a second reference voltage at the output, the first control input of reference voltage source being connected to one of the outputs of the probing pulse generator or to the processor output and the second control input of reference voltage being connected to the comparator output.

The basic technical task obtained as a result of realization of the invention is reduction of the storage elements necessary for the flaw detection of the pipeline of a given length (therefore, an increase of the distance controlled per pass of the inspection pig with a given volume of the data) and an increase of the accuracy of measurements and of the speed of the hardware data processing.

The mechanism of attaining said technical results consists in that the direct digital measurements of the ultrasonic pulse transit time in the pipe wall excludes measurement of the transit time of the ultrasonic pulse in the gap between the ultrasonic transducer and external wall of the pipeline and allows one to use the measuring means (digital counters of clock pulses) with a minimum word length of the output data permissible for an adequate accuracy of the measurements, therefore, already at the stage of measurements the scope of data at a given accuracy can be minimized.

Besides, the direct digital measurement of the transmit time of the ultrasonic pulses in the pipe wall allows the operations on hardware or software calculation of said time using the data on time of reception of the reflected pulses or on the data on the time of reception of the digital pulse amplitudes to be exclude.

The reflection of the ultrasonic pulses from the internal and external walls of the pipeline is accompanied by the appearance of a phase difference between the reflected ultrasonic pulses and the half-wave of positive polarity (relative to the potential in the absence of a pulse) for the first pulse corresponds to the half-wave of the opposite (negative) polarity (relative to the potential in the absence of a pulse) and vis versa. Depending on the amplifier adjustment and the conditions of distribution of the ultrasonic pulse, the amplitude of the negative half-wave of the second pulse can be disproportionately less than the amplitude of the positive half-wave of the first pulse, and the thickness measurement error associated with the phase difference can make 0.3–0.4 mm at the ultrasonic pulse frequency of 5 MHz.

The controlled reference voltage source allows the value of the reference voltage for the positive difference of the ultrasonic pulse reflected from the internal wall of the pipeline and the value of the reference voltage for the negative difference of the ultrasonic pulse reflected from the external wall of the pipeline to be compared. The connection of the control input of the reference voltage source to the comparator output allows the value set by the reference voltage source to be switched after the hardware identification of the arrival of the first ultrasonic pulse reflected from the internal wall of the pipeline that allows the measurement of the pipe wall thickness automatically eliminating the above error due to the phase difference.

In a preferable embodiment, the reference voltage source is capable of setting two values of the reference voltage of opposite polarity relative to the potential at the amplifer output in the absence of a pulse from the ultrasonic transducer corresponding to the reception of the ultrasonic pulse. The difference between the second value of the reference voltage (second threshold value) and the value of the potential at the amplifier output in the absence of the pulse from the ultrasonic transducer, corresponding to the reception of the ultrasonic pulse, is a maximum 0.8 and a minimum 0.2 magnitude of the difference between the first value of the reference voltage (first threshold value) and the potential value at the amplifier output in the absence of a pulse from the ultrasonic transducer corresponding to the reception of the ultrasonic pulse.

Because of a partial advance of the ultrasonic pulse through a media interface on the internal wall of the pipeline and a partial reflection of the ultrasonic pulse from a media interface on the external wall of the pipeline, the amplitude of the pulse reflected from the external wall of the pipeline is much less than the amplitude of the pulse reflected from the internal wall of the pipeline. If the second absolute threshold value is less than 0.2 of the first absolute threshold value, it is impossible to record two pulses in one comparator because of a gradual attenuation of the first pulse from the resonance in the ultrasonic transducer.

In the preferable embodiment the device further comprises a delay line, the comparator output being connected to the second control input of the reference voltage source through this delay line.

In another embodiment, the device further comprises a delay line, the comparator output is connected to the control input of a digital timer, and the control input of the digital timer is connected to the second control input of the reference voltage source through the delay line.

In the preferable embodiment of the device the delay line has an input of a delay period code, the input of the delay period code being connected to the processor output.

This embodiment of the device allows a reverse changeover of the comparator state due to a change in the threshold polarity to be avoided and, therefore, to generate a pulse of a duration adequate for starting the digital timer. Besides, at a strong attenuation of the electric pulses at the comparator input, the delay line allows the change of the comparator state (i.e. the stop of the digital timer) to be blocked during the attenuation of the first electric pulse from the resonance ultrasonic transducer.

In one of the embodiments the device further comprises a circuit for interlocking the change of state at the control input of the digital timer (or at the comparator output), said output being connected to the digital timer control input through said interlock circuit, said interlock circuit is connected to the second input of reference voltage source;

in the second embodiment of the invention the device includes a circuit for interlocking the change of state at the digital time control input (or at the comparator output), the comparator output being connected to the control input of the digital time and to the second input of reference voltage source though said interlock circuit;

in the third embodiment of the invention the device further comprises a preset length pulse shaper, the digital timer has an input for interlocking the count stop, the comparator output is connected to the triggering input of the preset length pulse shaper, the output of the preset length pulse shaper being connected to the input for interlocking the count stop of the digital timer.

In one preferable embodiment of the invention the device includes a trigger, the comparator output is connected to the digital timer control input through said trigger, the trigger input being connected to the second control input of reference voltage source;

or the device includes a trigger, the comparator output is connected to the digital timer control input and to the second control input of the reference voltage source though said trigger.

In the developed design the device is provided with a preset length pulse shaper, the trigger is made as in the form of a controlled lockable trigger and has a locking and state change input, the output of said trigger or comparator is connected to the triggering input of the preset length pulse shaper, the output of the preset length pulse shaper being connected to the input for interlocking the change of state of the controlled lockable trigger.

The interlocking of the comparator state output (or digital timer input) allows a false stop of the digital counter to be avoided because of the repeated switching of the comparator receiving a single ultrasonic pulse, which is possible because of a resonance character of operation of the ultrasonic transducer.

The device according to the above described embodiments includes a clock generator. The preset length pulse shaper is made as a digital counter with a complementing input, said complementing input of said counter being connected to the output of said clock generator, the triggering input of the preset length pulse shaper being made as a control input of the counter;

or the preset length pulse shaper is made as a digital counter with a complementing input, the complementing input of said counter is connected to the processor output, the triggering input of the preset length pulse shaper being made as a control input of the counter.

The preset length pulse shaper has a pulse length code input, said input being connected to the processor output.

This circuit with a preset length pulse shaper allows one to program the pulse shaping duration both directly before the diagnostic travel of the device and during its movement inside the pipeline according to a given program to provide effective identification of the ultrasonic pulses during on-line measurement of the time intervals between the pulses with the help of a single test line.

The digital timer includes the counter with a complementing input and clock generator, the digital timer control input is made as a control input of the counter, the clock generator output is connected to an accounting digital timer input;

or the digital timer includes a counter with a complementing input, the digital timer control input is made as a control input of the counter, the output of the processor being connected to the complementing input of the digital timer.

Still another embodiment of the device includes a differentiating circuit, the amplifier includes an output voltage limiter, the amplifier output is connected to the comparator input through said differentiating circuit, the processor output is connected to the probing pulse generator input. The time constant of the differentiating circuit is equal to 0.03–0.2 µs. The preferable resonance frequency of the ultrasonic transducers is 3 to 10 MHz.

The differentiating circuit provides conversion of the pulses from the amplifier in such a way that the amplitude of one half-wave of the pulse is much higher than the amplitude of the other half-wave of the pulse of opposite polarity relative to the potential at the amplifier output in the absence of pulses from the ultrasonic transducer. This allows false operation of the comparator to be excluded during the movement of the inspection pig inside the pipeline, when the amplitude of the half-wave of the pulse at the amplifier output preceding the calculated half-wave can exceed a threshold value along some length of the pipeline. The time constant within said limits provides incomplete differentiation of the pulse sufficient for organization of thresholds at an insignificant fall of the pulse amplitude. The connection of the probing pulse generator input to the processor output makes it possible to control the time intervals between the probing pulses and, respectively, the first reflected ultrasonic pulses both directly before the diagnostic travel and during the travel of the claimed device.

The reference voltage source has a code input of reference voltage set at the output, said input being connected to the processor output.

The reference voltage source may have a combined input for setting both a first and a second value of reference voltage at the output.

DETAILED DESCRIPTION OF THE PREFERRED EMBODIMENTS

The improvement of the ultrasonic inspection pigs (flaw detectors) allows an increase in the distance monitored per diagnostic pass and an increase in the data processing rate. As a result, an in-tube ultrasonic inspection pig (flaw detector) that can be used for inspection of pipelines with a nominal diameter from 10" up to 56" is provided.

The inspection pigs in preferable embodiments occupy about 85% of the nominal diameter of the pipeline and minimum passable turning radius of about 1.5 times the pipeline diameter. The inspection pigs operate at a pumped medium temperature of 0° C. to +50° C. and withstand the medium pressure of up to 80 atmospheres. The inspection pigs have explosion protection such as <<Explosion-proof body>> and <<Special explosion protection>> at an input electric current not exceeding 9 A.

Figure 1:
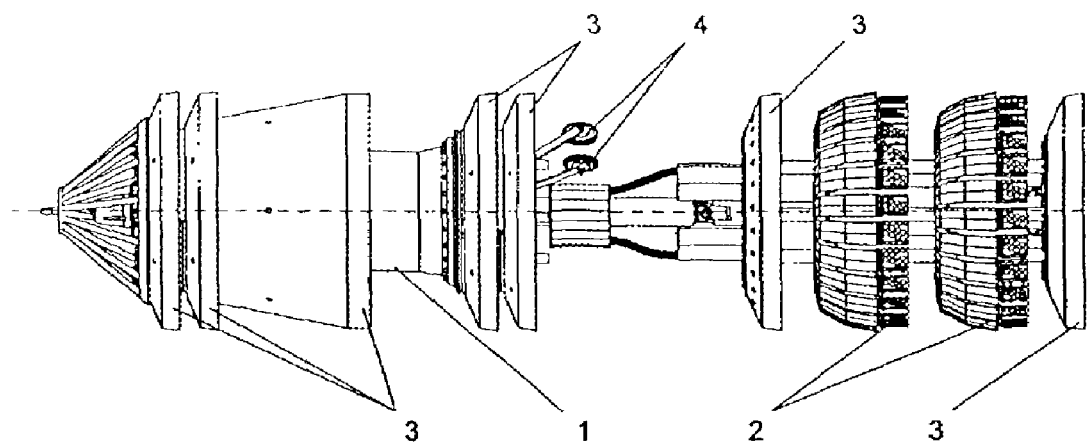
FIG. 1 illustrates a device for in-tube ultrasonic thickness metering in one design implementations.

The in-tube ultrasonic flaw detector for inspection of a pipeline having a diameter of 38" to 56" and a wall thickness of 4 to 23.5 mm in one preferable design embodiment shown in FIG. 1 includes: a housing 1, forming an explosion-proof shell incorporating a power supply and electronic equipment for measuring, processing and storage of the obtained measured data in an onboard computer controlling the operation of the inspection pig during its travel inside the pipeline. The power supply consists of storage batteries or galvanic cells with a capacity of up to 1000 ampere-hours.

The tail part of the inspection pig accommodates ultrasonic transducers 2 alternately emitting and receiving ultrasonic pulses. The polyurethane sealing rings 3 mounted on the inspection pig shell provide centering of the inspection pig inside the pipeline and its movement together with the fluid pumped through the pipeline. The wheels of the odometers 4 installed on the shell are pressed to the internal wall of the pipeline. During the travel of the inspection pig the information on the length of the passed way measured by the odometers is recorded in a storage module of the onboard computer and after the diagnostic travel and processing of the saved data allows one to determine the position of the flaws in the pipeline and, therefore, to locate the place of the subsequent excavation and repair of the pipeline.

Figure 2:
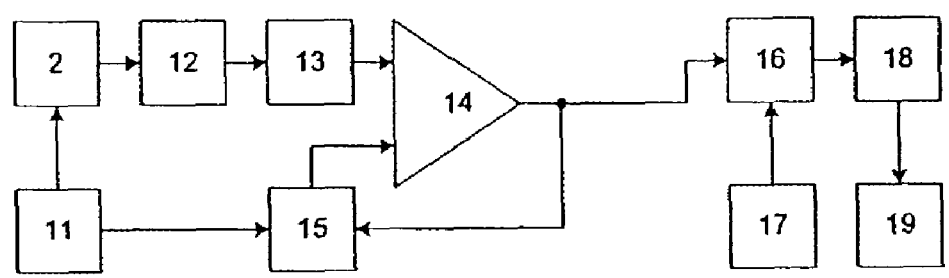
FIG. 2 is a diagram, illustrating the measurement of the transit time of the ultrasonic pulse in the pipe wall.

The electronic system of one simple inspection pig shown in FIG. 2 includes a probing pulse generator 11, a transducer 2, an amplifier 12, a differentiating circuit 13, a comparator 14, a digital counter 16, a processor 18, a data storage module 19, connected in series, as well as a reference voltage source 15 and a clock generator 17. The reference voltage source 15 has a first control input for setting a first value of reference voltage at the output and a second control input for setting a second value of reference voltage. The counter 16 has a control input and a complementing input. The comparator output 14 is connected to the control input of a counter 16. The output of the clock generator 17 is connected to the complementing input of the counter 16.

The output of the generator 11 is connected to the input of the ultrasonic transducer 2 whose output is connected to the input of the amplifier 12. One of the outputs (digital output) of the probing pulse generator 11 is connected to the first control input of reference voltage source 15 corresponding to setting the first value of reference voltage at the output of the source 15, the output of the comparator 14 is connected to the second control input of reference voltage source 15 corresponding to setting the second value of reference voltage at the output of the source 15. The output of reference voltage source 15 is connected to the input of threshold voltage of the comparator 14.

The device operates as follows.

Figure 3:
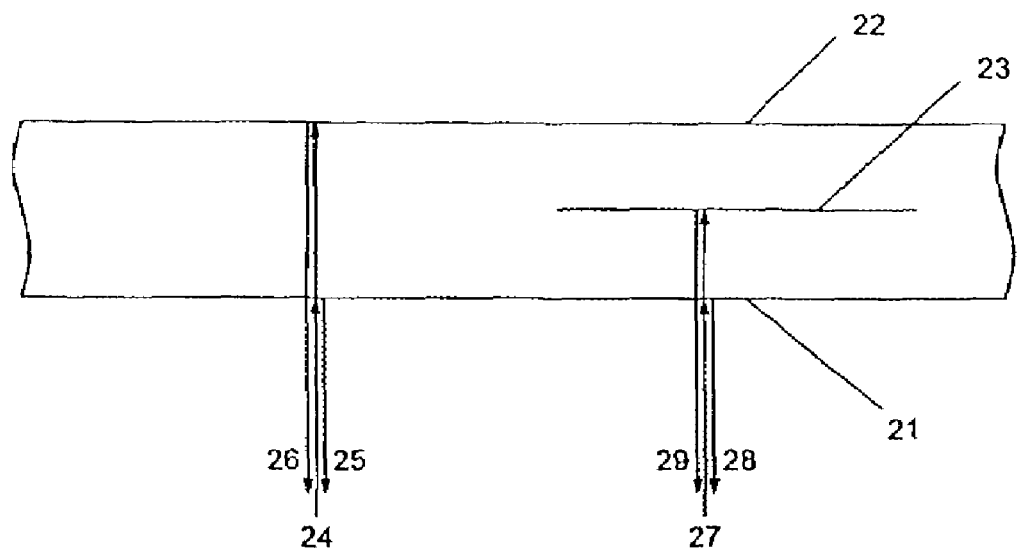
FIG. 3 is a diagram illustrating the path of the probing ultrasonic pulses along a flawless section of the pipe and along the section with a flaw such as "lamination"

The inspection pig is placed in the pipeline and the fluid medium (oil, oil product) is pumped through said pipeline. While the inspection pig moves inside the pipeline, the transducers periodically transmit ultrasonic pulses 24, 27 (FIG. 3) at a frequency of 5 MHz, which are partially reflected from the pipeline internal wall 21, external wall 22 or from the flaw area 23, for example, lamination of metal in the pipe wall. Having emitted the ultrasonic pulses, the transducers switch to the mode of reception of the reflected pulses and receive the pulses 25, 28 reflected from the internal wall, the pulses 26 reflected from the external wall or the pulses 29 reflected from said flaw area.

Figure 4:
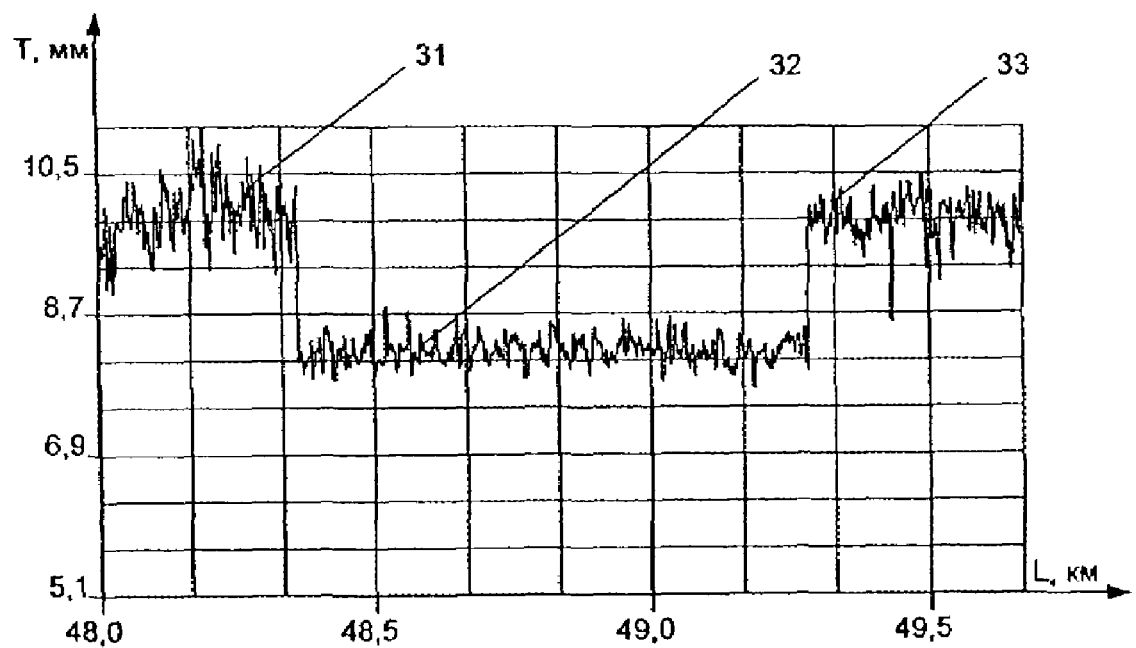
FIG. 4 illustrates the dependence of the wall thickness of the pipeline on the distance passed inside the pipeline along some length of the tested pipeline measured with the help of the present device.

FIG. 4 illustrates the measured dependence of the pipe wall thickness on the pipeline length. The sections 31, 32 and 33 in FIG. 4 correspond to the pipeline sections, in which pipes with a different nominal wall thickness are used: 10 mm for the section 31, 8.2 mm for the section 32 and 10 mm for the section 33.

After the inspection of a given length of the pipeline has been completed, the pig (flaw detector) is extracted from the pipeline and the data accumulated during the diagnostic pig travel are transferred to a separate computer.

The subsequent analysis of the recorded data allows one to identify flaws of the pipe wall and to determine their position on the pipeline for the purpose of subsequent repair of the faulty sections of the pipeline.

Figure 5:
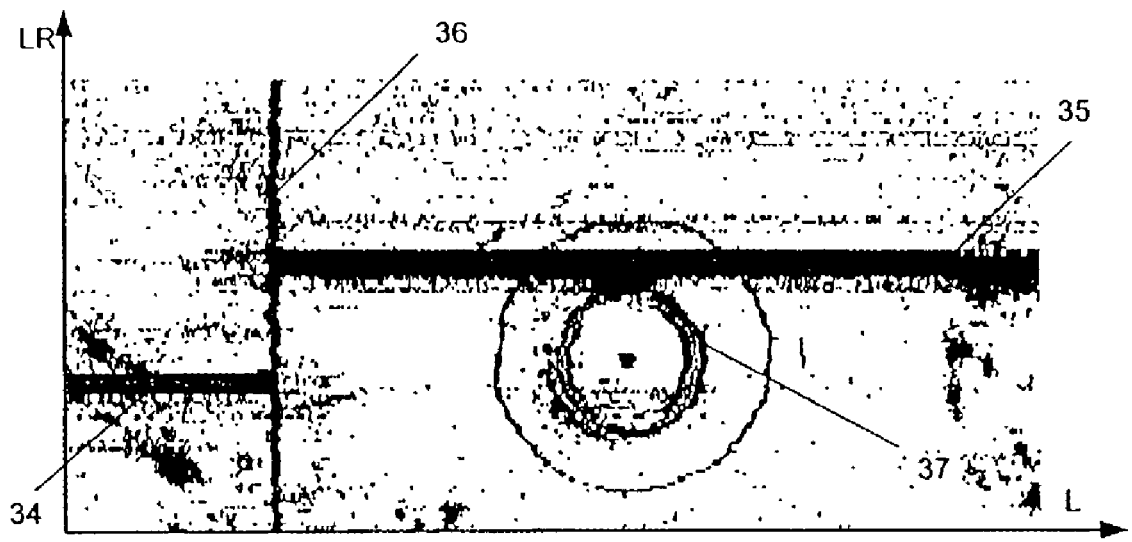
FIG. 5 is a graphic representation of the measured data on the wall thickness of the pipeline along some section of the tested pipeline allowing the welded joints to be identified.
Figure 6:
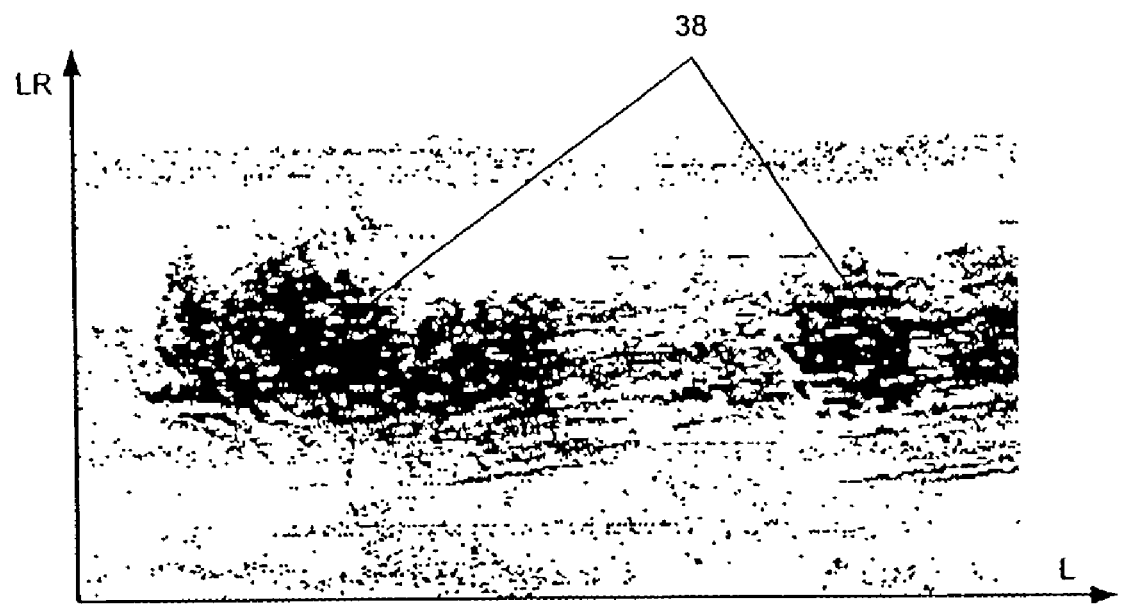
FIG. 6 is a graphic representation of the measured data on the pipe wall thickness for a section of the tested pipeline allowing the corrosion loss of metal to be identified.

FIGS. 5 and 6 illustrate the fragments of the graphic representation of the data obtained as a result of the diagnostic travel of the pig allowing the specific features of the pipeline and the wall flaws to be identified. The pipeline length along its axis is plotted on the axis L of FIGS. 5 and 6 and the length along its perimeter in the pipe cross section is plotted on the axis LR. The black dots on the image indicate that at this place the difference between the measured value of the wall thickness and the nominal value for the given section of the pipeline exceeds the preset threshold value. FIG. 5 illustrates the characteristic features of the pipelines: longitudinal weld joints 34 and 35 of the pipes, a weld joint between the pipes 36, and a plunger 37. Shown in FIG. 6 are typical corrosive flaws 38 on the pipe detected as a result of performing the in-tube ultrasonic flaw detection by the present method.

Figure 7:
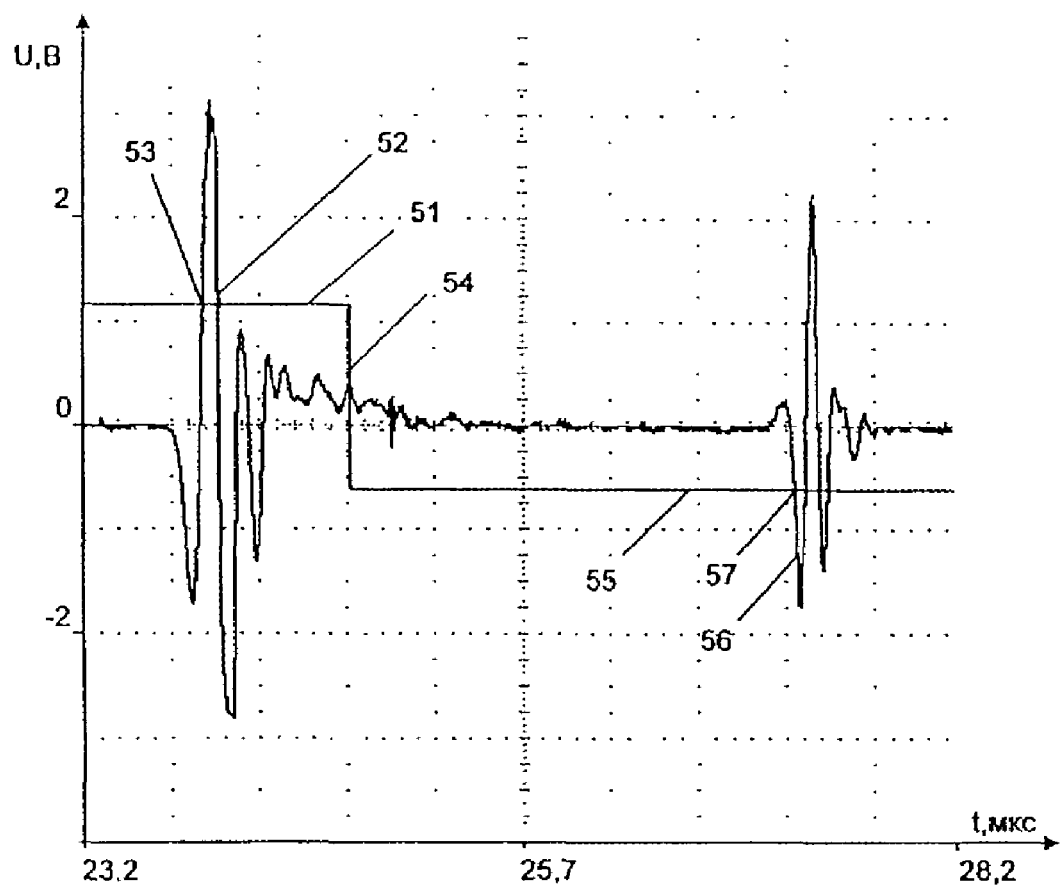
FIG. 7 illustrates the typical electric pulses at the output of the differentiating circuit corresponding to the reflected ultrasonic pulses.

The electric pulse corresponding to the first reflected ultrasonic pulse, triggers the counter 16 (FIG. 2) to count the transit time of the ultrasound in the wall of the pipeline; the pulse corresponding to the second reflected ultrasonic pulse stops the counter 16. The obtained data on the transit time of the ultrasonic pulses, as well as the data from other transducers including the odometers are converted in the processor 18 and recorded in the digital data storage module 19 of the onboard computer based on solid-state memory elements. The measurement of the transit time of the ultrasonic pulses in the pipeline wall is effected as follows. In a simple embodiment of the invention shown in FIG. 2 the inspection pig moves inside the pipeline and probing pulse generator 11 generates electric pulses with predetermined parameters that trigger the ultrasonic transducers 2, which emit ultrasonic pulses towards the pipeline wall. At the same time or with a certain delay, the pulse from the output of the generator 11 is applied to the control input of reference voltage source 15 to set the first reference voltage value (51) at the output of the source 15 (FIG. 7). Having emitted the ultrasonic pulses, the transducers 2 switch to reception of the reflected ultrasonic pulses. The transducers 2 receive the reflected ultrasonic pulses and generate output electric pulses which pass through the differentiating circuit 13. The typical pulses at the output of the differentiating circuit are shown in FIG. 7. The moment of reception of the first reflected ultrasonic pulse is determined by the time, when the positive half-wave 52 exceeds the threshold value 51 (instant 53). The state at the output of the comparator 14 (FIG. 2) changes, the counter 16 is triggered by the clock pulses from the clock generator 17, and a second threshold value 55 (FIG. 7) is established at the reference voltage input of the comparator. The moment of reception of the second ultrasonic pulse is determined, when the negative half-wave 56 of the second electric pulse achieves the second threshold value 55 (instant 57). The state at the output of the comparator 14 (FIG. 2) changes, the counter 16 stops, and the clock pulses accumulated in the counter 16 are transferred to the processor 18. In the processor 18 the data from different transducers are converted and recorded in the storage module 19. This embodiment of the device can effectively be used for recording the ultrasonic pulses corresponding to the electric pulses with a high attenuation factor, for example, for pulses in FIG. 7 at the first threshold value of −2 V and at the second threshold value 1.2 V. In the preferable embodiment the pulse conversion and recording circuit is built around microchips MAXIM910 and PLIS XILINX series 5000.

In the best embodiment of the device (FIG. 8), the electronic system includes:

a probing pulse generator 11, a transducer 2, an amplifier 12, a differentiating circuit 13, a comparator 14, a digital counter 16, a processor 18, a data storage module 19 connected in series, as well as a reference voltage source 15, a clock generator 17, a delay line 41 and a preset-length pulse shaper 42.

The counter 16 has a control input and an complementing input, and an input for interlocking the count stop. The output of the comparator 14 is connected to the control input of the counter 16.

The reference voltage source 15 has a first control input for setting a first reference voltage at the output of said source, a second control input control input for setting a second reference voltage at the output, and a input for setting reference voltage values at the output. The output of reference voltage source 15 is connected to the input of reference (threshold) voltage of the comparator 14.

The output of the clock generator 17 is connected to the complementing input of the counter 16. The output of the comparator 14 is connected to the second control input of reference voltage source 15 corresponding to setting the second value of reference voltage at the output of the source 15 through a delay line 41.

The shaper 42 is made in the form of a counter and has a control input for starting the pulse shaper, a complementing input and an input of a pulse length code. The input of the pulse length code of the shaper 42 is connected to the output of the processor 18.

The output of the comparator 14 is also connected to the input for starting the shaper 42, whose output is connected to the input for interlocking the count stop of the counter 16. The complementing input of the shaper is connected to one of the outputs of the clock generator 17.

The processor output 18 is connected to the probing pulse generator 11.

The output of the processor 18 is connected to the first control input of reference voltage source 15 corresponding to setting the first reference voltage at the output.

The delay line 41 has an input of a time delay code. The output of the processor 18 is connected to the input of the time delay code of the delay line.

Because of the delay line, the moment of change of the threshold 54 (FIG. 7) lags behind the moment 53 of recording the pulse. According to the program of operation of the processor 18 (FIG. 8) its output is used for setting the reference voltages at the output of reference voltage source 15, the delay of the delay line 41, and the length of the pulse generated by the shaper 42.

Figure 8:
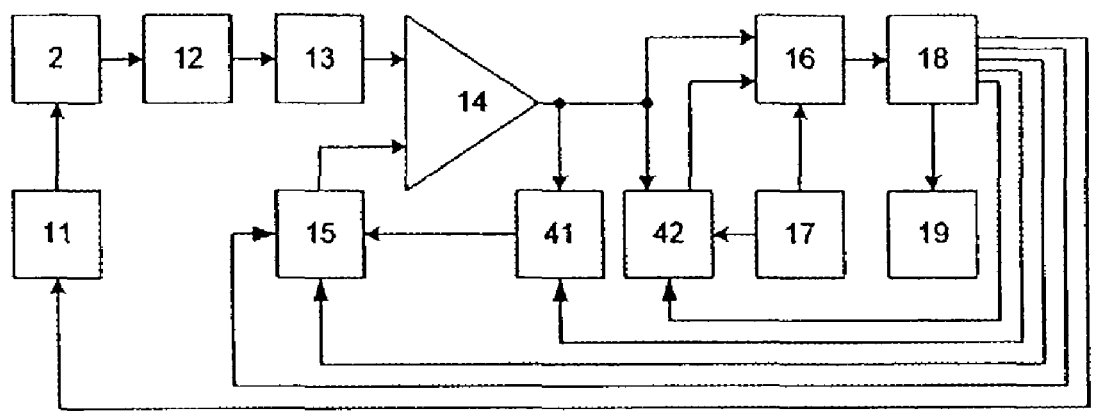
FIG. 8 is a diagram illustrating the measurement of the measurement of the transit time of the ultrasonic pulse in the pipe wall with a delay line and a preset length pulse shaper.

The output pulse of the processor acting on the control input of reference voltage source 15 (FIG. 8) results in producing a first value of reference voltage (0.8 V–1.2 V) at the output of the source 15. When recording the first electric pulse 52 (FIG. 7) at a respective change of state of the output of the comparator 14 (FIG. 8) a pulse is generated at the output of the shaper 42, which is applied to the input for interlocking the count stop of the counter 16. During the action of said pulse any change of state at the counter control input does not stop the counter 16. At the moment 54 (FIG. 7) a second value of reference voltage 55 (FIG. 7) (from −0.4 V to −0.6 V) is set at the reference voltage input of the comparator 14 (FIG. 8). After the lapse of time equal to duration of the pulse of the shaper 42 (FIG. 8), the counter 16 is ready to stop the count of clock pulses at a change of state at the control input. When recording the second electric pulse 52 (instant 57) (FIG. 7) and changing the state of the comparator 14 (FIG. 8), counter 16 stops and the number of clock pulses accumulated in the counter 16 is transferred to the processor 18. In the processor 18 the data from different transducers are converted and recorded in a data storage module 19 based on Flash or RAM memory elements.

In another embodiment of the device (FIGS. 9 and 10) the electronic system includes:

In another possible embodiment of the claimed device (FIGS. 9 and 10) the electronic system includes:

a probing pulse generator 11, a transducer 2, an amplifier 12, a differentiating circuit 13, a comparator 14, a trigger 43, a digital counter 16, a processor 18 and a data storage module 19, connected in series, as well as a reference voltage source 15 and a clock generator 17, a delay line 41 and a preset-length pulse shaper 42.

The counter 16 has a control input and a complementing input. The output of the comparator 14 is connected to the control input of the counter 16 through the trigger 43.

The output of the clock generator 17 is connected to the complementing input of the counter 16.

The reference voltage source 15 has a first control input for setting a first reference voltage at the output of reference voltage source, a second control input for setting a second reference voltage at the output, and an input of a value code for setting reference voltage values at the output. The output of the processor 18 is connected to the input of the value code for setting reference voltage values at the output The output of reference voltage source 15 is connected to the input of the reference (threshold) voltage of the comparator 14.

The output of the comparator 14 (FIG. 9) or the output of the trigger 43 (FIG. 10) is connected to the second control input of reference voltage source 15, corresponding to setting the second reference voltage at the output of the source 15, through a delay line 41.

The shaper 42 is made as a counter and has a control input for starting the shaper, a complementing input and an input of the pulse length code. The input of the pulse length code of the shaper 42 is connected to the output of the processor 18.

The trigger 43 has an input for interlocking the change of state of the trigger 43. The output or input of the trigger 43 is connected to the control input of for starting the shaper 42 whose output is connected to the input for interlocking the change of state of the trigger 43. The complementing input of the shaper being connected to one of the outputs of the clock generator 17.

The output of the processor 18 is connected to the input of the probing pulse generator 11.

The output of the processor 18 is connected to the first control input of reference voltage source 15 corresponding to setting the first reference voltage at the output.

The delay line 41 has an input of a time delay value code. The output of the processor 18 is connected to the input of the time delay value code of the delay line.

Due to the delay, the moment of change of the threshold 54 (FIG. 7) lags behind the moment 53 of recording the pulse. According to the program of operation of the processor 18 (FIG. 8) its output is used for setting a reference voltage at the output of reference voltage source 15, a delay of the delay line 41, and a length of the pulse generated by the shaper 42.

Figure 9:
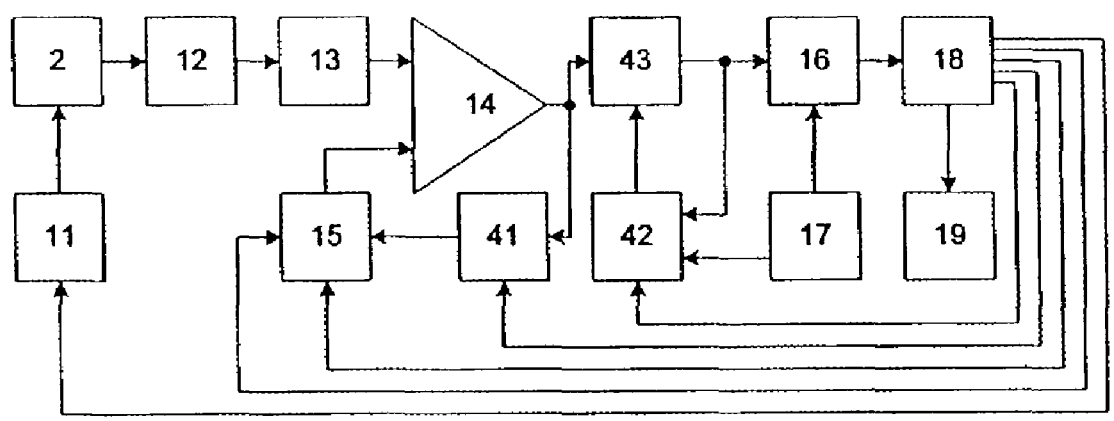
FIGS. 9 and 10 present a diagram illustrating the measurement of the transit time of the ultrasonic pulse in the pipe wall with a trigger, a delay line and a preset length pulse shaper.
Figure 10:
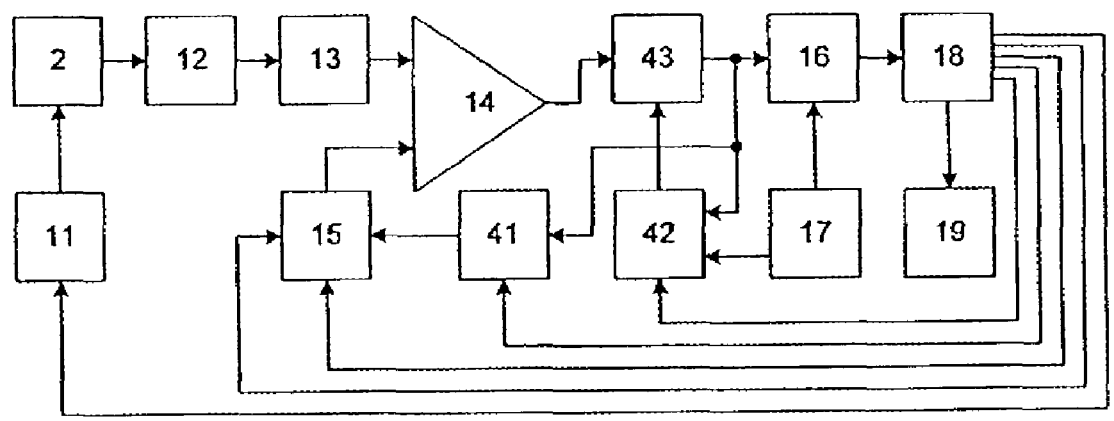

The output pulse of the processor acting on the control input of reference voltage source 15 generates a first value of reference voltage (0.8 V–1.2 V) at the output of the source 15. When recording the first electric pulse 52 (FIG. 7) and changing the output state of the comparator 14 (FIGS. 9 and 10), a pulse is generated at the output of the shaper 42, which is applied to the input for interlocking the change of state of the trigger 43. During the action of said pulse any change of state at the output of the comparator 14 does not stop the counter 16. At the moment 54 (FIG. 7) the second value of reference voltage 55 (FIG. 7) (−0.4 V to −0.6 V) is set at the reference voltage input of the comparator 14 (FIGS. 9 and 10). After the lapse of time equal to duration of the pulse of the shaper 42 (FIGS. 9 and 10), the counter 16 is ready to stop the count of clock pulses at a change of state at the control input of the comparator 14. When recording the second electric pulse 52 (instant 57) (FIG. 7) and changing the state of the comparator 14 (FIGS. 9 and 10)), the counter 16 stops, and the clock pulses accumulated in the counter 16 are transferred to the processor 18. In the processor 18 the data from different transducers are combined and recorded in the data storage module 19.

The invention of claimed is:

1. A device for intube ultrasonic thickness metering operating inside a tested pipeline and comprising a housing accommodating equipment for measurements, processing and storage of the measured data, said equipment including a probing pulse generator, an ultrasonic transducer, an amplifier, a comparator with an analog input, a digital timer, a processor and a data storage module connected in series; the device further comprises a controlled reference voltage source whose output is connected to the reference voltage input of said comparator, the reference voltage source is capable of setting at the output at least two values of reference voltage and has a first control input for setting a first reference voltage at the output and a second control input for setting a second reference voltage at the output, the first control input of reference voltage source being connected to one of the outputs of the probing pulse generator or to the processor output, the second control input of reference voltage being connected to the comparator output.

2. A device as claimed in claim 1, characterized in that the reference voltage source is capable of setting two values or reference voltage of opposite polarity relative to the potential at the amplifier output in the absence of pulses from the ultrasonic transducer corresponding to reception of an ultrasonic pulse.

3. A device as claimed in claim 1, characterized in that the magnitude of the difference between the second value of reference voltage and the potential value at the amplifier output in the absence of pulses from the ultrasonic transducer, corresponding .to the reception of the ultrasonic pulse, does not exceed 0.8 magnitude of the difference between the first value of reference voltage and the potential value at the amplifier output in the absence of pulses from the ultrasonic transducer corresponding to reception of ultrasonic pulses.

4. A device as claimed in claim 1, characterized in that it further comprises a delay line, the comparator output being connected to the second control input of reference voltage source through a delay line.

5. A device as claimed in claim 4, wherein the delay line has an input of delay period code, the input of the delay period code being connected to the processor output.

6. A device as claimed in claim 1, characterized in that: the comparator output is connected to the digital timer control input, the device further comprises a delay line, the digital timer control input being connected to the second control input of reference voltage source through a delay line.

7. A device as claimed in claim 1, characterized in that at further comprises a circuit for interlocking the change of state at the digital timer control input, the comparator output is connected to the digital timer control input through said interlock circuit, the second input at reference voltage source being connected to the input of said interlock circuit.

8. A device as claimed in claim 1, characterized in that it further comprises a circuit for interlocking the change of state at the digital timer control input, the comparator output being connected to the digital timer control input and to the second control input of the reference voltage source through said interlock circuit.

9. A device as claimed in claim 1, characterized in that it comprises a preset length pulse shaper, the digital timer has an input for interlocking the count stop, the comparator output is connected to the triggering input of a preset length pulse shaper, the output of the preset length pulse shaper being connected to the input for interlocking; the count stop of the digital timer.

10. The device as claimed in claim 9, further comprising a clock generator, the preset length pulse shaper is made as a digital counter with a complementing input, said complementing input of said counter is connected to the output of clock generator, the triggering, input of the preset length pulse simper being made as a control input of said counter.

11. The device as claimed claim 9, wherein the preset length pulse shaper is made as a digital counter with a complementing input, said complementing input of said counter is connected to the processor output, the triggering input of the preset length pulse shaper being made as a control input of the counter.

12. The device as claimed in claim 9, wherein the preset length pulse shaper has an input of the pulse length code, the input of the pulse duration code being connected to the processor output.

13. A device as claimed in claim 1, characterized in that comprises a trigger, the comparator output is connected to the digital timer control input through said trigger, the second control input of said reference voltage source being connected to the trigger input.

14. A device as claimed in claim 13, comprising a preset length pulse shaper, the trigger is made as a control led lockable trigger and has an interlocking and state change input, the comparator output is connected to an triggering input of the preset length pulse shaper, the output of the preset length pulse shaper is connected to the interlocking and state change input of the controlled lockable trigger.

15. A device as claimed in claim 13, comprising a preset length pulse shaper, the trigger is made as a controlled lockable trigger and has an interlocking and state change input, the output of the trigger is connected to the triggering input of the preset length pulse shaper, the output of the preset length pulse shaper being connected to the interlocking and state change input of the controlled lockable trigger.

16. A deice as claimed in claim 1, characterized in that it comprises a trigger, the comparator output is connected to the digital timer control input and to the second control input of the reference voltage source through said trigger.

17. A device as claimed in claim 1, characterized in that the digital timer includes a counter with a complementing input and a clock generator, the digital timer control input is made as a control input of said counter, the output of the cluck generator being connected to the complementing input of the counter.

18. A device as claimed in claim 1, characterized in that the digital timer includes a counter with a complementing input, the digital timer control input is made as a control input of said counter, the processor output being connected to the complementing input of said counter.

19. A device as claimed in claim 1, characterized in that it comprises a differentiating circuit, the amplifier includes an output voltage limiter, the amplifier output is connected to the comparator input through a differentiating circuit, the processor output being connected to an input of a probing pulse generator.

20. A device as claimed in claim 1, characterized in that reference voltage source has an input of a code of setting output values of reference voltage, said input being connected to the processor output.

* * * * *